(12) United States Patent
Kishita et al.

(10) Patent No.: US 8,191,402 B2
(45) Date of Patent: Jun. 5, 2012

(54) MONITORING DEVICE OF GAS INTRODUCING DEVICE FOR ANALYZER

(75) Inventors: Keisuke Kishita, Toyota (JP); Hisashi Sakai, Seto (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 440 days.

(21) Appl. No.: 12/523,370

(22) PCT Filed: Jul. 11, 2008

(86) PCT No.: PCT/JP2008/062963
§ 371 (c)(1),
(2), (4) Date: Jul. 16, 2009

(87) PCT Pub. No.: WO2009/011406
PCT Pub. Date: Jan. 22, 2009

(65) Prior Publication Data
US 2010/0077873 A1    Apr. 1, 2010

(30) Foreign Application Priority Data
Jul. 13, 2007   (JP) .................................. 2007-184696

(51) Int. Cl.
*G01N 1/22* (2006.01)
(52) U.S. Cl. ...................................... 73/23.42; 137/892
(58) Field of Classification Search .................. 73/23.42; 137/255, 266, 602, 892
See application file for complete search history.

(56) References Cited

U.S. PATENT DOCUMENTS

| 6,865,926 | B2 * | 3/2005 | O'Brien et al. | 73/23.27 |
| 7,201,179 | B2 * | 4/2007 | Barr et al. | 137/3 |
| 2006/0144126 | A1 * | 7/2006 | O'Brien et al. | 73/23.42 |
| 2007/0160325 | A1 * | 7/2007 | Son et al. | 385/37 |
| 2007/0194251 | A1 * | 8/2007 | Ward et al. | 250/492.21 |

FOREIGN PATENT DOCUMENTS

| EP | 2 166 345 | | 3/2010 |
| JP | 4-10349 | | 1/1992 |
| JP | 4-32144 | | 2/1992 |
| JP | 05134099 | A * | 5/1993 |
| JP | 05188019 | A * | 7/1993 |
| JP | 05196583 | A * | 8/1993 |
| JP | 5-64729 | | 9/1993 |
| JP | 5-332958 | | 12/1993 |

(Continued)

OTHER PUBLICATIONS

Extended European Search Report for EP Appl. No. 08778255.3 dated Aug. 2, 2010.

*Primary Examiner* — David Rogers
(74) *Attorney, Agent, or Firm* — Finnegan, Henderson, Farabow, Garrett & Dunner, LLP

(57) ABSTRACT

Gas is supplied from positive pressure ($10^5$ Pa or more) to an analyzer of high vacuum ($10^{-2}$ Pa or less) precisely and stably, while keeping conditions constant and replicating the conditions, and performing switching to a desired gas within a short time. According to a gas introducing device and a method, a plurality of types of gases are synthesized in a mixing chamber, the synthesized gas is introduced and is decompressed by a decompression pump to a pressure ranging from 0.1 Pa to 0.1 MPa, and the decompressed gas is introduced to a gas analyzer through a switching operation using a gas switching valve.

3 Claims, 2 Drawing Sheets

FOREIGN PATENT DOCUMENTS

| | | |
|---|---|---|
| JP | 8-68732 | 3/1996 |
| JP | 2571071 | 10/1996 |
| JP | 10-274644 | 10/1998 |
| JP | 2912105 | 4/1999 |
| JP | 11-183462 | 7/1999 |
| JP | 2001-50868 | 2/2001 |
| JP | 2003-340270 | 12/2003 |
| JP | 3888577 | 12/2006 |
| JP | 2007-101298 | 4/2007 |

* cited by examiner

MONITORING DEVICE OF GAS INTRODUCING DEVICE FOR ANALYZER

CROSS-REFERENCE TO RELATED APPLICATIONS

This application is a national phase application of International Application No. PCT/JP2008/062963, filed Jul. 11, 2008, and claims the priority of Japanese Application No. 2007-184696, filed Jul. 13, 2007, the contents of both of which are incorporated herein by reference.

TECHNICAL FIELD

The present invention relates to a gas component monitoring device used for a device that supplies gas with a pressure thereof regulated by a pressure regulating mechanism to an analyzer such as a TEM (Transmission Electron Microscope), a SEM (Scanning Electron Microscope), a XPS (X-ray Photoelectron Microscope), an AES (Auger Electron Spectroscopy), or an EPMA (Electron Probe Micro Analysis).

BACKGROUND ART

As a conventional technique of the present invention, Patent Document 1 describes "a X-ray diffraction device and a position sensitive gas-filled X-ray counter", for example.

FIG. 2 schematically illustrates the above-stated conventional X-ray diffraction device. Reference numeral 4 denotes a measurement chamber of a high vacuum atmosphere, inside of which a position sensitive gas-filled X-ray counter 5 is provided. Reference numeral 2 denotes a specimen. Incident X-ray 1 is incident to the specimen 2 in the direction of the arrow. The direction of diffracted X-ray 3 will be varied depending on the specimen, and when the specimen is a polycrystal, for example, the X-rays will be diffracted in a plurality of directions concurrently as illustrated in FIG. 2. The plurality of diffracted X-rays 3 is counted concurrently by the position sensitive X-ray counter 5.

The position sensitive X-ray counter 5 includes double-layered X-ray transmission windows 6 and 7 opposed to each other with a predetermined gap (e.g., 10 mm) therebetween, each having an arc shape (e.g., extending at the angle of)120° centered about a measurement position of the specimen, where an inside of the inner X-ray transmission window 7 (a first window) is called a counter portion 11, and an inside of the outer X-ray transmission window 6 (a second window) is called a vacuum vessel portion 10. The X-ray transmission window 6 is made of a high-polymer organic film of 2.5 µm in thickness, and the X-ray transmission window 7 is made of a beryllium film of 7.5 µm in thickness. An operation gas is filled in the counter portion 11, and electrodes 8 and 9 are disposed therein.

Reference numeral 22 denotes a plurality of gas cylinders, from which a plurality of gases are introduced to a gas mixer 21 via decompression valves to set the composition of gas. Reference numeral 18 denotes a pressure regulator including a pressure indicator, a variable leak valve and a controller not illustrated. In accordance with a difference between a preset pressure and a measurement pressure by the pressure indicator not illustrated, the controller performs PID (proportional-plus-integral-plus-derivative) control to open/close a variable leak valve 19 so as to regulate conductance, thus supplying the operation gas to the counter portion 11 while keeping a gas pressure constant. Reference numeral 20 denotes a rotary pump. The pressure can be controlled by regulating the variable leak valve 19 and a gain and a time constant of the controller in the pressure regulator 18. That is, the operation gas composition and the pressure control (regulating) mechanism are used so as to adjust the counter efficiency of the X-ray counter and the X-ray transmittance to be optimal values in accordance with the energy of the X-ray measured.

The vacuum vessel portion 10 is evacuated by a turbo molecular pump 14 and a rotary pump 15. Reference numeral 16 denotes a vacuum gage, based on which if the pressure of the vacuum vessel portion 10 is higher than a preset threshold because of breakage of the X-ray transmission window 7, a closing valve 17 is closed automatically, thus preventing leakage of the operation gas to the measurement chamber 4 of a high vacuum atmosphere.

When air is to be leaked to the counter portion 11, the vacuum vessel portion 10, or the measurement chamber 4 of a high vacuum atmosphere, the leaking has to be conducted while keeping the pressures of the counter portion 11, the vacuum vessel portion 10 and the measurement chamber 4 equal so as to prevent the breakage of the X-ray transmission windows 6 and 7. To this end, the valve 17 is firstly closed to shut off the supply of the operation gas and reduce the pressure of the counter portion, followed by opening of the valves 23, 24, and 25 to make the pressures of the portions 11, 10 and 4 equal, and then the leak valve 26 is opened so as to introduce dry air passing through an air drier 27. In this operation, in order to minimize a differential pressure applied to the X-ray transmission windows 6 and 7, attention has to be paid so as to make conductance from the leak valve 26 to both surfaces of the X-ray transmission windows 6 and 7 equal.

Patent Document 1: JP Published Patent Application No. 05-332958 A (1993)

DISCLOSURE OF THE INVENTION

In the above-stated conventional technique, the specimen is disposed in a high vacuum atmosphere. On the other hand, since an actual material is used in an environment different from such an atmosphere, a disparity will occur between the analysis result under high vacuum and the state of the actual material. Thus, it is desired to introduce gas to the analyzer at a position where the specimen is disposed. However, since the inside of the gas analyzer is under high vacuum ($10^{-2}$ Pa or less), the gas pressure has to be controlled thereto from a positive pressure ($10^5$ Pa or more) that differs by seven digits, and therefore it is not easy to achieve a target pressure and to keep the achieved pressure constant, it takes time to change the type of gas completely, and it is not easy to replicate the same condition. Thus, the difficulty arises in conducting analysis under the same conditions by a stable pressure operation and in performing reanalysis by replicating the same conditions.

It is an object of the invention to, in the invention filed earlier by the present Applicant (Japanese Patent Application No. 2007-183292), monitor an introduced gas component and feed back the same, thus controlling an introduced gas and to feed back a pressure in an analyzer to control a pressure regulating portion, thus keeping, changing and replicating a pressure condition in the analyzer.

In order to cope with the above-stated problems, a gas component monitoring device of the present invention is used for a gas introducing device for an analyzer, the gas component monitoring device monitoring a gas component in the gas introducing device. The gas introducing device includes: a gas synthesis portion that synthesizes a plurality of types of gases in a mixing chamber; a pressure regulating portion that introduces the gas synthesized in the gas synthesis portion and decompresses the gas; a gas switching portion including a gas switching valve that performs switching so as to introduce the decompressed gas from the pressure regulating portion to the analyzer, and a gas analyzer that analyses a component of the synthesized gas. The gas synthesis portion includes a plurality of gas introducing paths leading from a plurality of gas sources to the mixing chamber via a pressure valve, a path for exhaustion from the mixing chamber to exterior via an open/close valve, and a path for introduction from the mixing chamber to the pressure regulating portion via a flow-control valve. The pressure regulating portion includes an introducing chamber that introduces gas from the gas synthesis portion, a path provided with a pump that decompresses the gas introduced in the introducing chamber to a pressure ranging from 0.1 Pa to 0.1 MPa, and a path leading from the introducing chamber to the gas switching portion. The gas switching portion includes a path guiding the gas from the pressure regulating portion to the analyzer via the gas switching valve, and a path for exhaustion to exterior via a pump.

In addition to the above-stated features, the gas component monitoring device of the present invention is used for a gas introducing device for analyzer, the gas component monitoring device monitoring a gas component in the gas introducing device. The gas introducing device includes a gas controlling portion. The gas controlling portion controls the pressure valve of the gas synthesis portion so as to regulate the gas synthesized in the gas synthesis portion in accordance with a gas component analysis result from the gas component monitoring device, controls the pump of the pressure regulating portion so as to allow the pressure regulating portion to decompress the introduced gas to a desired pressure, and switches the gas switching valve to supply a desired type of gas to the analyzer.

In addition to the above-stated features, the gas component monitoring device of the present invention is used for a gas introducing device for analyzer, the gas component monitoring device monitoring a gas component in the gas introducing device and feeding back a gas introducing condition to the gas introducing device. The gas switching valve of the gas introducing device guides a desired gas to the analyzer through a desired path among a plurality of paths.

According to the present invention, in the above-stated gas introducing device, the gas component in the gas introducing device is monitored so as to feed back a gas introducing condition, whereby when a change in substance under a gas atmosphere is analyzed for an analyzer of a high vacuum atmosphere, a desired gas can be generated precisely and can be supplied stably, whereby an on-the-spot analysis is enabled while keeping the same conditions and replicating the conditions.

According to the present invention, in order to respond to needs of analyzing a change in material structure at a nano-level because higher-functionally materials are developed, atmosphere required can be controlled precisely to satisfy the needs, thus contributing to precise analysis of material behavior.

BEST MODE FOR CARRYING OUT THE INVENTION

The following describes an embodiment of the present invention with reference to the drawings.

Figure 1:
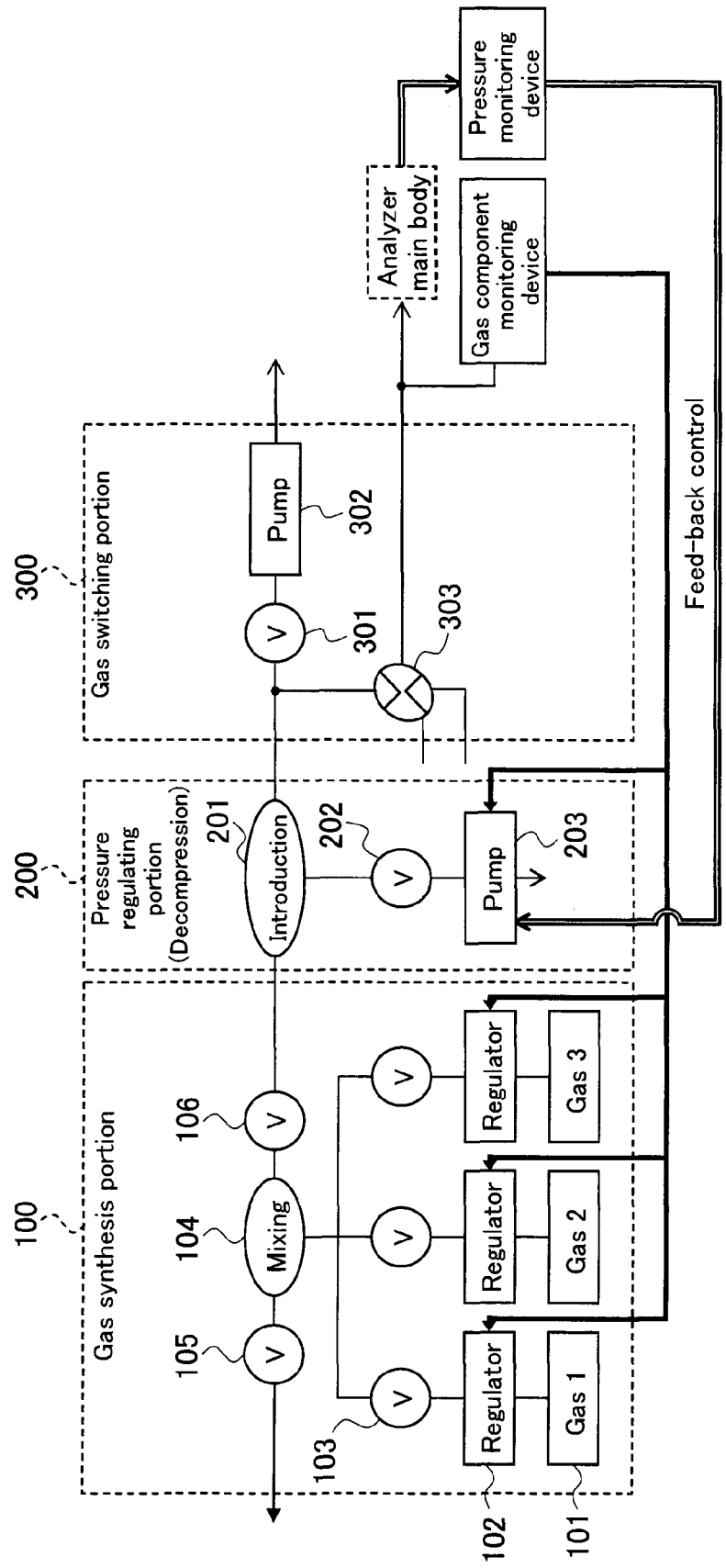
FIG. 1 illustrates the overall configuration of arrangement of a gas introducing device for analyzer and a gas component monitoring device according to the present invention.
Figure 2:
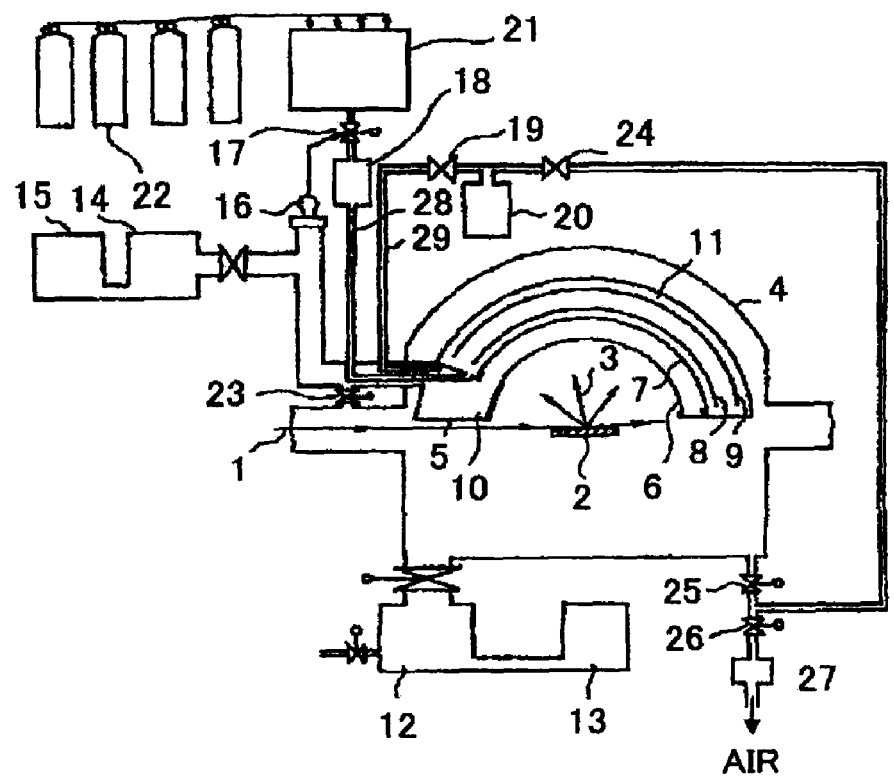
FIG. 2 schematically illustrates a conventional X-ray diffraction device.

FIG. 1 illustrates the overall configuration of a gas introducing device for an analyzer according to the present invention. As illustrated in FIG. 1, the gas introducing device of the present invention includes a gas synthesis portion 100, a pressure regulating portion 200 and a gas switching portion 300.

The gas synthesis portion 100 includes a gas supply source 101 such as a gas cylinder, a regulator 102, a valve 103, a mixing chamber 104, and valves 105 and 106. Pressure of a gas supply source 101 each filled with a different type of gas is a high pressure of about 16 MPa, from which gas is introduced to the mixing chamber 104 through the regulator 102 and the valve 103 so as to synthesize gas of a desired gas component. Pressure of the gas in the mixing chamber 104 is about 0.2 to 0.4 Mpa.

The gas synthesized in the mixing chamber is introduced to an introducing chamber 201 in the pressure regulating portion 200 via the flow-control valve 106. The flow rate in this case is 100 cc/min or less. The introducing chamber is connected with a decompression pump 203 via a valve 202, by which gas in the introducing chamber 201 is decompressed to about 0.1 Pa to 0.1 MPa. If necessary, the pressure regulating portion 200 may be configured with a plurality of stages. In such a case, the introduced gas may be decompressed finally to about 0.1 Pa to 0.1 MPa at the final stage of the pressure regulating portion.

In the above-stated device, when the component of the gas synthesized in the gas synthesis portion is changed, inert gas is introduced from a gas supply source 101 filled with the inert gas, followed by opening of the valve 105, the valves 106 and 301 are further opened, and a pump 302 in the gas switching portion 300 is driven. In this way, old gas in a gas supply line from the mixing chamber to a switching valve 303 is exhausted using the inert gas. Then, the valve 105 is closed, and new gas is introduced to the mixing chamber, thus replacing the inert gas in the gas supply line with the new gas.

In this way, the old gas in the mixing chamber is replaced with the inert gas within a few seconds and the new gas is synthesized with a few minutes, thus starting the supply of the new gas to the gas analyzer.

As the above-stated gas line, a plurality of lines may be provided, such as an oxide line, a reducing line, and an inert line in accordance with types of gases to be synthesized, and a desired gas may be supplied to the analyzer by the operation of the gas switching valve 303 provided in the gas switching portion.

The gas switching valve 303 switches a path appropriately so that a desired gas can be supplied to the analyzer main body. The introduction line to the analyzer main body includes a gas component monitoring device, and in accordance with the gas component information monitored by the gas component monitoring device, the valve 103 of the gas introduced to the mixing chamber is adjusted, thus regulating the gas component synthesized in the mixing chamber.

Industrial Applicability

The present invention is applicable to a gas component monitoring device used for a device that supplies gas with a pressure thereof regulated by a pressure regulating mechanism to an analyzer such as a TEM, a SEM, a XPS, an AES, or an EPMA.

The invention claimed is:

1. A gas component monitoring device for monitoring components of the gas that has been synthesized in a gas introducing device for an analyzer, the gas introducing device comprising:

a gas synthesis portion that synthesizes a plurality of types of gases in a mixing chamber; a pressure regulating portion that introduces the gas synthesized in the gas synthesis portion and decompresses the gas; a gas switching portion including a gas switching valve that performs switching so as to introduce the decompressed gas from the pressure regulating portion to the analyzer, and a gas analyzer that analyses a component of the synthesized gas, wherein the gas synthesis portion comprises a plurality of gas introducing paths leading from a plurality of gas sources to the mixing chamber via a pressure valve, a path for exhaustion from the mixing chamber to exterior via an open/close valve, and a path for introduction from the mixing chamber to the pressure regulating portion via a flow-control valve, the pressure regulating portion comprises an introducing chamber that introduces gas from the gas synthesis portion, a path provided with a pump that decompresses the gas introduced in the introducing chamber to a pressure ranging from about 0.1 Pa to 0.1 MPa, and a path leading from the introducing chamber to the gas switching portion, and the gas switching portion comprises a path guiding the gas from the pressure regulating portion to the analyzer via the gas switching valve, and a path for exhaustion to exterior via a pump.

2. The gas component monitoring device for monitoring components of the gas that has been synthesized in a gas introducing device for an analyzer according to claim 1, wherein the gas introducing device comprises a gas controlling portion, wherein the gas controlling portion controls the pressure valve of the gas synthesis portion so as to regulate the gas synthesized in the gas synthesis portion in accordance with a gas component analysis result from the gas component monitoring device, controls the pump of the pressure regulating portion so as to allow the pressure regulating portion to decompress the introduced gas to a desired pressure, and switches the gas switching valve to supply a desired type of gas to the analyzer.

3. The gas component monitoring device for monitoring components of the gas that has been synthesized in a gas introducing device for an analyzer according to claim 1, wherein the gas switching valve guides a desired gas to the analyzer through a desired path among a plurality of paths.

* * * * *